(12) United States Patent
Zhang et al.

(10) Patent No.: US 7,582,738 B2
(45) Date of Patent: Sep. 1, 2009

(54) DIAGNOSTIC ASSAY FOR WISKOTT-ALDRICH SYNDROME AND GENETICALLY RELATED DISORDERS

(75) Inventors: Kejian Zhang, Cincinnati, OH (US); Richard J. Wenstrup, Cincinnati, OH (US); Alexandra H. Filipovich, Covington, KY (US)

(73) Assignee: Children's Hospital Medical Center, Cincinnati, OH (US)

( * ) Notice: Subject to any disclaimer, the term of this patent is extended or adjusted under 35 U.S.C. 154(b) by 144 days.

(21) Appl. No.: 11/295,149

(22) Filed: Dec. 6, 2005

(65) Prior Publication Data

US 2006/0134673 A1 Jun. 22, 2006

Related U.S. Application Data

(60) Provisional application No. 60/637,410, filed on Dec. 17, 2004.

(51) Int. Cl.
*C07H 19/00* (2006.01)
*C12Q 1/68* (2006.01)
*C12P 19/34* (2006.01)
*C07H 21/04* (2006.01)

(52) U.S. Cl. .................. 536/22.1; 536/24.33; 435/6; 435/91.2

(58) Field of Classification Search ............ 536/23.1, 536/24.33; 435/6
See application file for complete search history.

(56) References Cited

U.S. PATENT DOCUMENTS

| 5,858,673 | A | 1/1999 | Price |
| 6,068,974 | A | 5/2000 | Klann |
| 6,270,977 | B1 | 8/2001 | Klann |
| 6,762,021 | B2 | 7/2004 | Tokunaga |
| 6,790,952 | B2 | 9/2004 | Groen |

FOREIGN PATENT DOCUMENTS

WO    PCT/US05/44956    5/2007

OTHER PUBLICATIONS

Hagemann, TL et al. The identification and characterization of two promoters and the complete sequence for the Wiskott-Aldrich syndrome gene. Biochem and Biophy Research Communications, vol. 256, pp. 104-109, 1999.*
Abu-Amero et al. A Novel Splice Site Mutation in the WAS gene causes Wiskott Aldrich syndrome in two siblings of a Saudi family, Blood Coagul Fibrinolysis, Oct. 2004,599-603, v15-7, copyright 2004, Lippincott Williams & Wilkins.
Hageman et al " The Identification and Characterization of Two Promoters and the Complete Genomic Sequence for the Wiskott-Aldrich Syndrome Gene", Biochemical and Biophysical Research Communications 1999, p. 104-109 v256, c 1999 Academic Press, USA.
Abu-Amero et al. A Novel Splice Site Mutation in the WAS gene causes Wiskott Aldrich syndrome in two siblings of a Saudi family, Blood Coagul Fibrinolysis, Oct. 2004,599-603, v15-7.
Jiang et al [Identification of two novel WASP gene mutations in 3 boys with Wiskott-Aldrich Syndrome] Zhonghua Er Ke Za Zhi Aug. 2003; 590-593, v41(8) Abstract.

* cited by examiner

*Primary Examiner*—Suryaprabha Chunduru
(74) *Attorney, Agent, or Firm*—Taft Stettinius & Hollister LLP (57) ABSTRACT

The methods and compositions of the invention find use in the clinical diagnosis of primary immunodeficiencies, particularly Wiskott-Aldrich related syndromes. The compositions of the invention include isolated nucleic acid molecules and oligonucleotide pairs suitable for use in amplifying regions of the Wiskott-Aldrich syndrome protein gene and in determining the nucleotide sequence of the Wiskott-Aldrich syndrome protein gene in a patient. The invention facilitates efficient, cost-effective amplification of one or more regions of the Wiskott-Aldrich syndrome protein gene. The nucleotide sequence of amplified DNA comprising one or more regions of the Wiskott-Aldrich Syndrome Protein gene can be determined using the methods and compositions of the invention. Knowledge of the patient's nucleotide sequence in the Wiskott-Aldrich Syndrome Protein gene allows diagnosis of the patient's primary immunodeficiency.

5 Claims, 1 Drawing Sheet

FIG. 1

DIAGNOSTIC ASSAY FOR WISKOTT-ALDRICH SYNDROME AND GENETICALLY RELATED DISORDERS

CROSS-REFERENCE TO RELATED APPLICATIONS

This application claims priority to, and the benefit of U.S. Provisional Patent Application No.: 60/637,410, filed on Dec. 17, 2004, which is incorporated herein by reference in its entirety.

FIELD OF THE INVENTION

The field of this invention relates to the field of genetic diagnostic assays for primary immunodeficiencies.

BACKGROUND OF THE INVENTION

Primary immunodeficiency is a group of diseases that have been increasingly recognized in both children and adults. These diseases, such as Wiskott-Aldrich Syndrome; X-linked hyper IgM syndrome, X-linked lymphoproliferative disease, Severe combined immunodeficiency, X-linked agammaglobulinemia; and Familial hemophagocytic lymphohistiocytosis secondary to perforin 1 and Munc 13-4 mutations, can be difficult to clinically define. Recently, mutation detection has been chosen as the definitive diagnostic criterion for these life-threatening diseases by the Pan-American Group for Immunodeficiency and the European Society for Immunodeficiency.

Wiskott-Aldrich syndrome (WAS) is a rare, X-linked inherited disorder of platelets and immune cells due to deficiency of an intracellular protein, WASP (Wiskott-Aldrich syndrome protein). The Wiskott-Aldrich syndrome protein functions in the normal structure and function of most blood cells. WASP deficiency leads to low platelet counts often associated with small platelet size. Patients exhibit a significant risk of bleeding as well as susceptibility to bacterial, viral, or fungal infections. The differential diagnosis of Wiskott-Aldrich Syndrome includes immune thrombocytopenic purpura (ITP), X-linked congenital neutropenia (XLN), and X-linked thrombocytopenia (XLT). Worldwide, Wiskott-Aldrich Syndrome affects three per million males. Patients with incomplete forms of the disease may survive into adulthood, but most patients die by age 15.

The WASP gene is located on the short arm of the X chromosome at p11.22-p11.23. Previously available mutation detection assays include linkage studies, single-strain confirmation polymorphism (SSCP), and X-inactivation studies. These assays are either less sensitive or time-consuming. Therefore, development of efficient, accurate, sensitive methods of detecting mutations in the genes associated with primary immunodeficiencies, particularly Wiskott-Aldrich syndrome is desirable.

SUMMARY OF THE INVENTION

Compositions and methods for diagnosing Wiskott-Aldrich related syndromes are provided. The inventions are based on identification of nucleotide sequences for amplifying and sequencing the exons and exon-intron boundaries of the Wiskott Aldrich Syndrome (WAS) protein gene. The compositions of the invention allow amplification of the WAS protein gene exons and exon-intron boundaries by one set of amplification conditions thus minimizing labor and equipment requirements. Further, use of the compositions of the invention allow determination of the nucleotide sequence of the amplified WAS protein gene exons and exon-intron boundaries. The WAS protein gene exon and exon-intron boundary nucleotide sequences provide diagnostic information for Wiskott-Aldrich related syndromes.

Compositions of the invention include isolated nucleic acid molecules comprising the nucleotide sequences set forth in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:21, and SEQ ID NO:22, and variants thereof. Variant nucleotide sequences of the invention differ by one nucleotide alteration from the nucleotide sequences set forth in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:21, and SEQ ID NO:22, or hybridize under stringent conditions to a complement of a nucleotide sequence of the invention.

Compositions of the invention further include oligonucleotide pairs comprising a first nucleic acid molecule and a second nucleic acid molecule. Oligonucleotide pairs of the invention allow amplification of a region of the Wiskott-Aldrich syndrome protein gene. Nucleotide sequences of the first nucleic acid molecule in an oligonucleotide pair are set forth in SEQ ID NO:1, SEQ ID NO:3, SEQ ID NO:5, SEQ ID NO:7, SEQ ID NO:9, SEQ ID NO:11, SEQ ID NO:21, and variants thereof. Nucleotide sequences of the second nucleic acid molecule in an oligonucleotide pair are set forth in SEQ ID NO:2, SEQ ID NO:4, SEQ ID NO:6, SEQ ID NO:8, SEQ ID NO:10, SEQ ID NO:12, SEQ ID NO:22, and variants thereof. In an embodiment, an oligonucleotide pair of the invention comprises a first nucleic acid molecule having the nucleotide sequence set forth in SEQ ID NO:1 or a variant thereof and a second nucleic acid molecule having the nucleotide sequence set forth in SEQ ID NO:2 or a variant thereof. In an embodiment, an oligonucleotide pair of the invention comprises a first nucleic acid molecule having the nucleotide sequence set forth in SEQ ID NO:3 or a variant thereof and a second nucleic acid molecule having the nucleotide sequence set forth in SEQ ID NO:4 or a variant thereof. In an embodiment, an oligonucleotide pair of the invention comprises a first nucleic acid molecule having the nucleotide sequence set forth in SEQ ID NO:5 or a variant thereof and a second nucleic acid molecule having the nucleotide sequence set forth in SEQ ID NO:6 or a variant thereof In an embodiment, an oligonucleotide pair of the invention comprises a first nucleic acid molecule having the nucleotide sequence set forth in SEQ ID NO:7 or a variant thereof and a second nucleic acid molecule having the nucleotide sequence set forth in SEQ ID NO:8 or a variant thereof. In an embodiment, an oligonucleotide pair of the invention comprises a first nucleic acid molecule having the nucleotide sequence set forth in SEQ ID NO:9 or a variant thereof and a second nucleic acid molecule having the nucleotide sequence set forth in SEQ ID NO:10 or a variant thereof. In an embodiment, an oligonucleotide pair of the invention comprises a first nucleic acid molecule having the nucleotide sequence set forth in SEQ ID NO:11 or a variant thereof and a second nucleic acid molecule having the nucleotide sequence set forth in SEQ ID NO:12 or a variant thereof. In an embodiment, an oligonucleotide pair of the invention comprises a first nucleic acid molecule having the nucleotide sequence set forth in SEQ ID NO:21 or a variant thereof and a second nucleic acid molecule having the nucleotide sequence set forth in SEQ ID NO:22 or a variant thereof.

In an embodiment, the invention provides a method of amplifying a region of the Wiskott-Aldrich syndrome protein gene. The method comprises the steps of obtaining a biological sample from a human subject and performing enzymatic amplification using an oligonucleotide pair of the invention. In an aspect of the invention, the method provides the step of performing enzymatic amplification using a first oligonucleotide pair of the invention. In an aspect of the invention, the method provides the step of performing enzymatic amplification using a second oligonucleotide pair of the invention. In an aspect of the invention, the method provides the step of performing enzymatic amplification using a third oligonucleotide pair of the invention. In an aspect of the invention, the method provides the step of performing enzymatic amplification using a fourth oligonucleotide pair of the invention. In an aspect of the invention, the method provides the step of performing enzymatic amplification using a fifth oligonucleotide pair of the invention. In an aspect of the invention, the method provides the step of performing enzymatic amplification using a sixth oligonucleotide pair of the invention. Enzymatic amplification using a first, second, third, fourth, fifth, and sixth oligonucleotide pair may share the same amplification conditions.

In an embodiment, the invention provides a method of determining the nucleotide sequence of a region of the Wiskott-Aldrich syndrome protein gene of a human subject. The method comprises the steps of obtaining a biological sample from the human subject, performing enzymatic amplification of a region of the Wiskott-Aldrich syndrome protein gene, and using an isolated nucleic acid molecule of the invention in a sequencing reaction. The nucleotide sequence of the isolated nucleic acid molecule is selected from the group set forth in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:21, SEQ ID NO:22, and variants thereof.

In an embodiment, the invention provides a method of diagnosing a Wiskott-Aldrich related syndrome. The method comprises the steps of obtaining a biological sample from a human subject, performing enzymatic amplification of a region of the Wiskott-Aldrich syndrome protein gene, determining the nucleotide sequence of the amplified region or regions, and comparing the nucleotide sequence with a standard sequence profile. In an aspect of the method, at least one oligonucleotide pair of the invention amplifies a region of the Wiskott-Aldrich syndrome protein gene. The method provides enzymatic amplification of multiple regions of the Wiskott-Aldrich syndrome protein gene using identical incubation conditions. In an aspect determining the nucleotide sequence comprises the step of using an isolated nucleic acid molecule of the invention in a sequencing reaction. The nucleotide sequence of one or more amplified regions of the Wiskott-Aldrich syndrome protein gene is determined. In an aspect the nucleotide sequence of the Wiskott-Aldrich syndrome protein gene exons and exon-intron boundaries is determined. In an aspect of the invention the Wiskott-Aldrich related syndrome is selected from the group consisting of Wiskott-Aldrich Syndrome, leukopoietic disorders, X-linked thrombocytopenia, immune thrombocytopenic purpura, and X-linked congenital neutropenia.

DETAILED DESCRIPTION OF THE INVENTION

Figure 1:
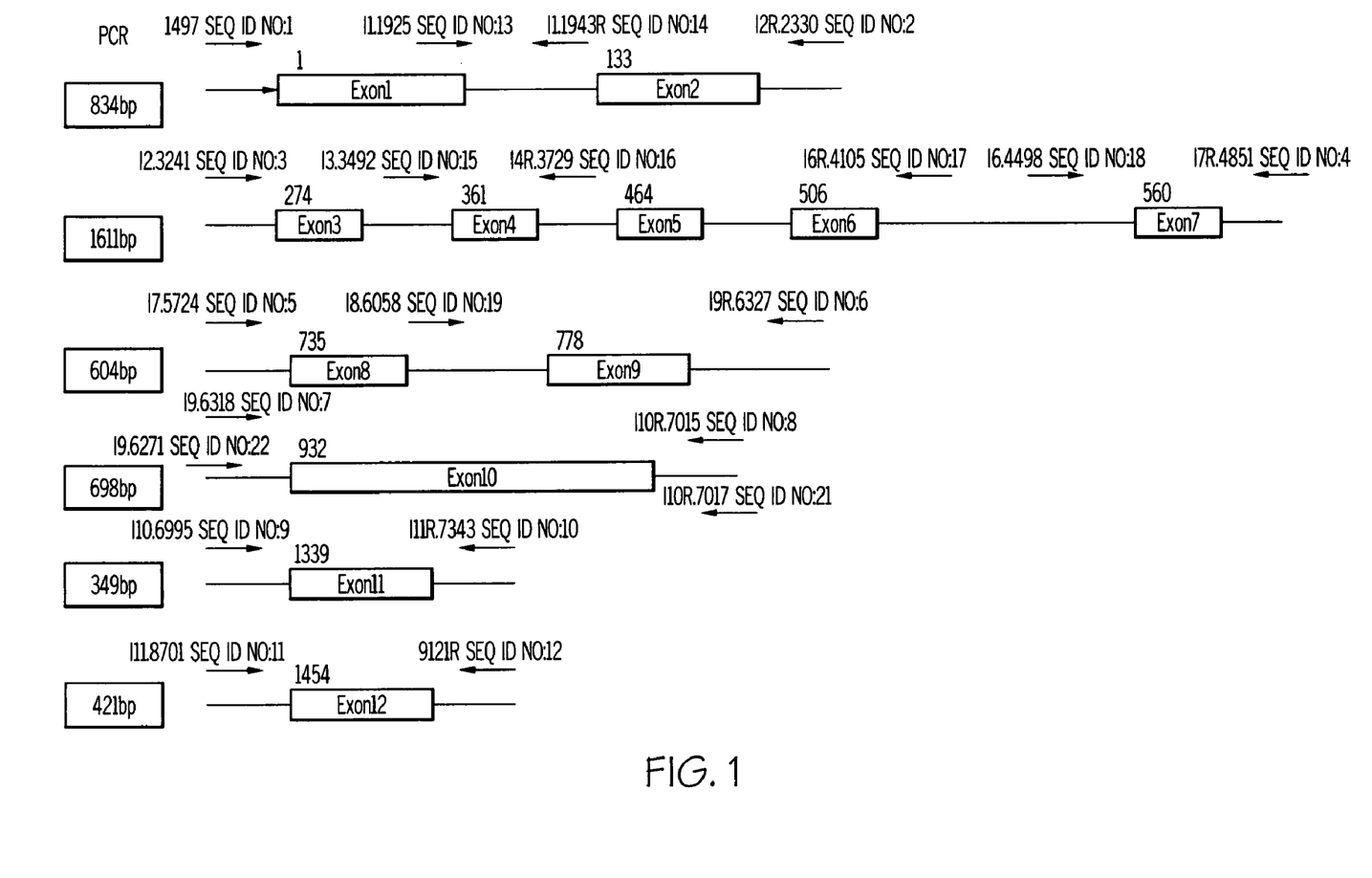
FIG. 1 presents a schematic of the amplification and sequencing test design for the Wiskott-Aldrich Syndrome Protein gene. Amplification primers are indicated by arrows and the amplification primer name is indicated. Additional sequencing primers are indicated by arrows and the sequencing primer name. The nucleotide sequence of the primers is set forth in the sequence listing. The size of the amplified region of the Wiskott-Aldrich Syndrome Protein gene is indicated at the left. Regions containing exons are indicated with open boxes while other regions are indicated with a solid line.

The present invention provides methods of diagnosing a primary immunodeficiency, particularly a Wiskott-Aldrich related syndrome such as, but not limited to, Wiskott-Aldrich Syndrome. The invention provides methods of amplifying a region or regions of the Wiskott-Aldrich Syndrome protein gene, and methods of determining the nucleotide sequence of a region or regions of the Wiskott-Aldrich Syndrome protein gene. Compositions of the invention include isolated nucleic acid molecules and oligonucleotide pairs useful in amplifying a region or regions of the Wiskott-Aldrich Syndrome protein gene as well as kits comprising isolated nucleic acid molecules of the invention. The invention relates to methods of efficiently amplifying multiple regions of the Wiskott-Aldrich Syndrome protein gene. The invention allows direct sequencing of the entire coding region and intron/exon boundaries of the WAS gene.

Wiskott-Aldrich related syndromes are primary immunodeficiencies characterized by low-platelet counts and small platelet size. Wiskott Aldrich related syndromes include, but are not limited to, Wiskott-Aldrich Syndrome, immune thrombocytopenic purpura (ITP), X-linked thrombocytopenia (XLT), leukopoietic disorders, and X-linked congenital neutropenia. Wiskott-Aldrich related syndromes have been difficult to diagnose clinically. The symptoms associated with Wiskott-Aldrich related syndromes include, but are not limited to, melena, draining ears, eczema, thrombocytopenia, IgG2 deficiencies, diarrhea, recurrent infections particularly recurrent respiratory infections, poor antibody response to polysaccharide antigens, cutaneous anergy, partial T-cell immunodeficiency, elevated levels of IgE and IgA, low levels of IgM, hypercatabolism of IgG but normal IgG levels, small platelets, elevated susceptibility to infection, pallor, malaise, malnutrition, distended abdomen, rashes, vesicles, pyoderma, eczema, petechiae, alopecia, telangiectasia, conjunctivitis, pyogenic infections, bleeding manifestations, and increased splenic destruction of platelets.

Compositions of the invention include isolated nucleic acid molecules having the nucleotide sequences set forth in SEQ ID NO:1, 2, 3, 4, 5, 6, 7, 8, 9, 10, 11, 12, 13, 14, 15, 16, 17, 18, 19, 21, and 22 or a fragment or variant thereof. The nucleic acid molecules of the invention anneal to the Wiskott Aldrich syndrome protein gene (SEQ ID NO:20). The invention encompasses isolated or substantially purified nucleic acid compositions. An "isolated" or substantially "purified" nucleic acid molecule, or biologically active portion thereof, is substantially free of other cellular material, or culture medium when produced by recombinant techniques or substantially free of chemical precursors or other chemicals when chemically synthesized.

By fragments or variants thereof is intended isolated nucleic acid molecules having a nucleotide sequence that differs by one nucleotide alteration from that set forth in SEQ ID NO:1, 2, 3, 4, 5, 6, 7, 8, 9, 10, 11, 12, 13, 14, 15, 16, 17, 18, 19, 21, and 22 or a nucleotide sequence that hybridizes under stringent conditions to a complement of SEQ ID NO:1, 2, 3, 4, 5, 6, 7, 8, 9, 10, 11, 12, 13, 14, 15, 16, 17, 18, 19, 21, and 22. A fragment or variant that differs by one nucleotide alteration from a nucleotide sequence set forth in SEQ ID NO:1, 2, 3, 4, 5, 6, 7, 8, 9, 10, 11, 12, 13, 14, 15, 16, 17, 18, 19, 21, or 22 differs from that nucleotide sequence by the addition, insertion, deletion, removal, subtraction, or substitution of one nucleotide. Fragments or variants include isolated nucleic acid molecules having a nucleotide sequence that hybridizes under stringent conditions to a complement of SEQ ID NO:1, 2, 3, 4, 5, 6, 7, 8, 9, 10, 11, 12, 13, 14, 15, 16, 17, 18, 19, 21, or 22.

By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing).

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m$=81.5° C.+16.6(log M)+0.41(% GC)−0.61(% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, N.Y.); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

Compositions of the invention include oligonucleotide pairs. An oligonucleotide pair of the invention consists of a first isolated nucleic acid molecule of the invention and a second isolated nucleic acid molecule of the invention with different nucleotide sequences. An oligonucleotide pair of the invention is suitable for use as a primer pair or primer set in a PCR reaction. In an embodiment, an oligonucleotide pair comprises a first nucleic acid molecule having the nucleotide sequence set forth in SEQ ID NO:1, 3, 5, 7, 9, 11, 21, or a fragment or variant thereof and a second nucleic acid molecule having the nucleotide sequence set forth in SEQ ID NO:2, 4, 6, 8, 10, 12, 22, or a fragment or variant thereof. In an embodiment, an oligonucleotide pair comprises a first nucleic acid molecule having the nucleotide sequence set forth in SEQ ID NO:1 or a fragment or variant thereof and a second nucleic acid molecule having the nucleotide sequence set forth in SEQ ID NO:2 or a fragment or variant thereof. In an embodiment, an oligonucleotide pair comprises a first nucleic acid molecule having the nucleotide sequence set forth in SEQ ID NO:3 or a fragment or variant thereof and a second nucleic acid molecule having the nucleotide sequence set forth in SEQ ID NO:4 or a fragment or variant thereof. In an embodiment, an oligonucleotide pair comprises a first nucleic acid molecule having the nucleotide sequence set forth in SEQ ID NO:5 or a fragment or variant thereof and a second nucleic acid molecule having the nucleotide sequence set forth in SEQ ID NO:6 or a fragment or variant thereof. In an embodiment, an oligonucleotide pair comprises a first nucleic acid molecule having the nucleotide sequence set forth in SEQ ID NO:7 or a fragment or variant thereof and a second nucleic acid molecule having the nucleotide sequence set forth in SEQ ID NO:8 or a fragment or variant thereof. In an embodiment, an oligonucleotide pair comprises a first nucleic acid molecule having the nucleotide sequence set forth in SEQ ID NO:9 or a fragment or variant thereof and a second nucleic acid molecule having the nucleotide sequence set forth in SEQ ID NO:10 or a fragment or variant thereof. In an embodiment, an oligonucleotide pair comprises a first nucleic acid molecule having the nucleotide sequence set forth in SEQ ID NO:11 or a fragment or variant thereof and a second nucleic acid molecule having the nucleotide sequence set forth in SEQ ID NO:12 or a fragment or variant thereof. In an embodiment, an oligonucleotide pair comprises a first nucleic acid molecule having the nucleotide sequence set forth in SEQ ID NO:21 or a fragment or variant thereof and a second nucleic acid molecule having the nucleotide sequence set forth in SEQ ID NO:22 or a fragment or variant thereof. Additional oligonucleotide pairs comprising the isolated nucleic acid molecules of the invention are encompassed by the invention. The first and second nucleic acid molecules of an oligonucleotide pair anneal to opposite strands of the WASP gene such that they allow amplification of a region of the WASP gene bracketed by the primer pair.

By "amplification" is intended an increase in the amount of nucleic acid molecules in a sample. Amplifying DNA increases the amount of acid precipitable nucleic acid molecules. The amount of acid precipitable material increases by 1%, 5%, 10%, 15%, 20%, 25%, 30%, 35%, 40%, 45%, 50%, 55%, 60%, 65%, 70%, 75%, 80%, 85%, 90%, 95%, 100%, 150%, 200%, 250%, or more. Methods of quantifying nucleic acid molecules are known in the art and include, but are not limited to, UV absorption spectra, radiolabel incorporation, agarose gel electrophoresis, and ethidium bromide staining. See, for example, Ausubel et al., eds. (2003) *Current Protocols in Molecular Biology*, (John Wiley & Sons, New York) and Sambrook et al. (2001) *Molecular Cloning: A Laboratory Manual* (3d ed., Cold Spring Harbor Laboratory Press, Plainview, N.Y., herein incorporated by reference.

Enzymatic amplification is the process of using enzymes to perform amplification. A common type of enzymatic amplification is the polymerase chain reaction (PCR). Known methods of PCR include, but are not limited to, methods using paired primers, nested primers, single specific primers, degenerate primers, gene-specific primers, vector-specific primers, partially-mismatched primers, and the like. Known methods of PCR include, but are not limited to, methods using DNA polymerases from extremophiles and engineered DNA polymerases. It is recognized that it is preferable to use high fidelity PCR reaction conditions in the methods of the invention. See also Innis et al., eds. (1990) PCR Protocols: A Guide to Methods and Applications (Academic Press, New York); Innis and Gelfand, eds. (1995) PCR Strategies (Academic Press, New York); and Innis and Gelfand, eds. (1999) PCR Methods Manual (Academic Press, New York).

Methods of performing enzymatic amplification, particularly PCR, are known in the art and discussed elsewhere herein. Known PCR methods include but are not limited to a series of incubation periods or cycles at predetermined temperatures. Various methods of controlling the duration and temperature of each incubation period are known in the art and include, but are not limited to, the use of thermocyclers and transfer between baths at predetermined temperatures. It is envisioned that any means of controlling the PCR reaction incubation conditions may be used in the practice of the invention. In an embodiment a thermocycler is used to regulate the PCR incubation conditions of the enzymatic amplification. By "incubation conditions" is intended the temperature and duration of each incubation period in the enzymatic amplification. In an embodiment the invention provides oligonucleotide pairs that will amplify multiple regions of the WASP gene in multiple reactions that are performed under similar incubation conditions. By using similar incubation conditions multiple enzymatic amplification reactions can be performed in one thermocycle chamber simultaneously. The invention reduces the thermocycler resources required for enzymatic amplification of the Wiskott-Aldrich Syndrome Protein gene.

In PCR, typically multiple cycles of a series of incubation periods are performed. Often a single incubation period precedes the cycled incubation period series. The cycle incubation conditions of the incubation period series are designed to facilitate denaturation of the template DNA, annealing of the primer to the template DNA, and extension of the template bound primer. Various factors such as, but not limited to, the primer nucleotide sequence, the template nucleotide sequence, and the type of DNA polymerase can be used to predict suitable temperatures and durations of the incubation periods. An example of incubation conditions suitable for use with the oligonucleotide pairs of the invention is described elsewhere herein. It is recognized that multiple suitable incubation temperatures and durations exist and that the invention is not limited to the precise incubation descriptions described elsewhere herein. In an embodiment, the temperature of the annealing incubation is in the range of 54° C. to 59° C., particularly 57° C.

The human Wiskott-Aldrich Syndrome Protein gene is located on the short arm of the X chromosome at p11.22-p11.23. The human genomic sequence (SEQ ID NO:20) spans 9481 nucleotides in 12 exons. The Wiskott-Aldrich Syndrome family of proteins appears to be involved in signal transduction from the cell surface to the actin cytoskeleton. Mutations in the Wiskott Aldrich Syndrome protein gene result in Wiskott Aldrich Syndrome which is characterized by immunodeficiencies and microthrombocytopenia. Considerable clinical variation exists among Wiskott Aldrich Syndrome patients, and mutation detection is considered essential for accurate diagnosis and prognostic determinations. The oligonucleotide pairs of the invention allow amplification of the exons and exon-intron boundaries of the Wiskott-Aldrich Syndrome protein gene.

Another indication that nucleotide sequences are substantially identical is if two molecules hybridize to each other under stringent conditions. Generally, stringent conditions are selected to be about 5° C. lower than the thermal melting point ($T_m$) for the specific sequence at a defined ionic strength and pH. However, stringent conditions encompass temperatures in the range of about 1° C. to about 20° C. lower than the $T_m$, depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

By "region" is intended a portion of the entire nucleotide sequence of interest, such as the genomic WASP gene. A region or fragment of the entire nucleotide sequence of interest, such as the genomic WASP gene may range from 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 349, 350, 360, 370, 380, 390, 400, 410, 420, 421, 430, 440, 450, 460, 470, 480, 490, 500, 510, 520, 530, 540, 550, 560, 570, 580, 590, 600, 604, 610, 620, 630, 640, 650, 660, 670, 680, 690, 698, 700, 710, 720, 730, 740, 750, 760, 770, 780, 790, 800, 810, 820, 830, 834, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1100, 1150, 1200, 1250, 1300, 1350, 1400, 1450, 1500, 1550, 1600, 1611, 1650, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300, 5400, 5500, 5600, 5700, 5800, 5900, 6000, 6100, 6200, 6300, 6400, 6500, 6600, 6700, 6800, 6900, 7000, 7100, 7200, 7300, 7400, 7500, 7600, 7700, 7800, 7900, 8000, 8100, 8200, 8300, 8400, 8500, 8600, 8700, 8800, 8900, 9000, 9100, 9200, 9300, 9400, or 9481 nucleotides, or up to the total number of nucleotides on the short arm of the human X chromosome between p11.22 and p11.23. Such a region contains nucleotide sequence from one or more WASP gene exons, one or more WASP gene introns, or the regulatory control region operably linked to the WASP gene. The oligonucleotide pairs of the invention amplify various regions of the WASP gene. The oligonucleotide pair having the nucleotide sequences set forth in SEQ ID NOS:1 and 2 allows amplification of a region of the WASP gene comprising exons 1 and 2. The oligonucleotide pair having the nucleotide sequences set forth in SEQ ID NOS:3 and 4 allows amplification of a region of the WASP gene comprising exons 3, 4, 5, 6, and 7. The oligonucleotide pair having the nucleotide sequences set forth in SEQ ID NOS:5 and 6 allows amplification of a region of the WASP gene comprising exons 8 and 9. The oligonucleotide pair having the nucleotide sequences set forth in SEQ ID NOS:7 and 8 allows amplification of a region of the WASP gene comprising exon 10. The oligonucleotide pair having the nucleotide sequences set forth in SEQ ID NOS:21 and 22 allows amplification of a region of the WASP gene comprising exon 10. The oligonucleotide pair having the nucleotide sequences set forth in SEQ ID NOS:9 and 10 allows amplification of a region of the WASP gene comprising exon 11. The oligonucleotide pair having the nucleotide sequences set forth in SEQ ID NOS:11 and 12 allows amplification of a region of the WASP gene comprising exon 12.

By "biological sample" is intended a sample collected from a subject including, but not limited to, tissues, cells, mucosa, fluid, scrapings, hairs, cell lysates, and secretions. Biological samples such as blood samples can be obtained by any method known to one skilled in the art.

The invention further provides methods of determining the nucleotide sequence of a region or regions of the WASP gene. The method involves obtaining a biological sample from a human subject, performing enzymatic amplification of a region of the WASP gene, providing amplified DNA of a region of the WASP gene, and using an isolated nucleic acid molecule of the invention in a sequencing reaction. It is recognized that an embodiment of the invention involves obtaining a biological sample from a human subject, performing enzymatic amplification of a region of the WASP gene, providing amplified DNA of a region of the WASP gene, and using microarray sequence analysis to determine the nucleotide sequence of a region or regions of the WASP gene.

By "amplified DNA" is intended the product of enzymatic amplification.

Any method of DNA sequencing known in the art that utilizes a primer of predetermined sequence can be used in the methods of the invention. Methods of sequencing DNA are known in the art and are described in Graham & Hill eds. (2001) *DNA Sequencing Protocols* (Humana Press, Totowa N.J.), Kieleczawa ed (2004) *DNA Sequencing: Optimizing the Process and Analysis* (Jones & Bartlett Publishers, Ontario), Ausubel et al., eds. (2003) *Current Protocols in Molecular Biology*, (John Wiley & Sons, New York) and Sambrook et al. (2001) *Molecular Cloning: A Laboratory Manual* (3d ed., Cold Spring Harbor Laboratory Press, Plainview, N.Y., herein incorporated by reference in their entirety). Any method of DNA sequencing known in the art that utilizes a resequencing microarray can be used in the methods of the invention. Methods of microarray sequencing DNA are known in the art and are described in Warrington et al. (2002) *Hum Mutat* 19:402-409 and Cutler et al. (2001) *Genome Res* 11:1913-1925, herein incorporated by reference in their entirety.

A method of the invention involves the step of comparing the nucleotide sequence of a region of a subject's Wiskott-Aldrich Syndrome Protein gene with a standard sequence profile. Such comparison may be performed by any means known in the art including, but not limited to, manually, electronically, and automatically. It is recognized that the comparison may be performed by a person or machine.

By "standard sequence profile" is intended a listing of the consensus nucleotide sequence of at least one nucleotide sequence of interest. A standard sequence profile may contain additional information including but not limited to, a correlation of at least one nucleotide sequence variation with a disease, syndrome, prognosis, or treatment protocol. A standard sequence profile may exist in printed or electronic form, a remotely accessible form, in a database, or in any other means known in the art. In an embodiment a standard sequence profile is a Wiskott-Aldrich Syndrome standard sequence profile. For instance, an exemplary Wiskott-Aldrich Syndrome standard sequence profile correlates certain nucleotide alterations in the Wiskott-Aldrich syndrome protein gene with a Wiskott-Aldrich related syndrome.

In an embodiment, the invention provides kits for performing the methods of the invention. Such kits comprise an isolated nucleic acid molecule of the invention, particularly multiple isolated nucleic acid molecules of the invention, and an oligonucleotide pair of the invention, particularly multiple oligonucleotide pairs of the invention, yet more particularly six oligonucleotide pairs of the invention. A kit of the invention may further comprise a description of an enzymatic amplification protocol suitable for use with an oligonucleotide pair of the invention. Additionally a kit of the invention may comprise a listing of the consensus Wiskott Aldrich Syndrome Protein gene nucleotide sequence in paper or electronic form or a means of accessing a consensus WASP gene nucleotide sequence. A kit of the invention may comprise a resequencing microarray chip comprising segments of the WASP gene nucleotide sequence.

A kit of the invention may comprise an enzymatic amplification reaction component. By "reaction component" is intended any substance that facilitates the indicated reaction. Reaction components that facilitate the reaction may or may not participate in the chemical processes of the reaction. Reaction components include, but are not limited to, vessels, such as microfuge tubes and multiwell plates; measuring devices, such as micropipette tips and capillary tubes; filters; separation devices such as microfuge tube filter inserts, vacuum apparati, purification resins, magnetic beads, and columns; reagents; compounds; solutions; molecules; buffers; inhibitors; chelating agents; ions; terminators; stabilizers; precipitants; solubilizers; acids; bases; salts; reducing agents; oxidizing agents; enzymes; catalysts; and denaturants. In an embodiment of the invention, concentrated reaction components are provided in kits of the invention. The concentration of the reaction components provided in a kit of the invention may be 1, 2, 3, 4, 5, 6, 7, 8, 9, 10, 15, 20, 25, 30, 35, 40, 50, 60, 70, 80, 90, 100, or more fold concentrated than the desired concentration of the component in the reaction. Reagents and reaction level concentrations of various reagents are discussed elsewhere herein.

The following examples are offered by way of illustration and not limitation.

EXPERIMENTAL

Example1

Extraction of DNA from Whole Blood

Puregene DNA isolation kit (Gentra Systems, Minneapolis, Minn., USA) was used for genomic DNA isolation from blood and other tissues. All reagents were provided by the kit. Whole blood was collected from a patient. The blood was collected in EDTA tubes or ACD tubes to prevent the blood from clotting and to reduce DNA degradation. Fresh blood samples were stored at 2-8° C. for up to 7 days. In some instances whole blood was frozen immediately and stored frozen until use.

Enucleated red blood cells were removed from the whole blood sample by lysis. Red blood cell lysis solution (9 ml) was placed in a 15 ml tube. Two to three ml of whole blood were added to the red blood cell lysis solution. The tube contents were mixed by inversion and incubated for 10 minutes at room temperature. The tube was centrifuged for 10 minutes at 2,400 rpm.

The supernatant was removed leaving a visible white pellet containing white blood cells and residual fluid. The pellet was resuspended in the residual fluid by vigorous vortexing.

Cell lysis solution (3 ml) was added to the resuspended cells. The tube was inverted 15-20 times. When cell clumps remained, the tubes were placed in a 37° C. water bath overnight. If cell clumps persisted, 15 µl proteinase K was added and the tube was incubated at 55° C. for one hour to overnight. Samples were stored in cell lysis solution for up to 18 months at room temperature.

Proteins were precipitated by the addition of protein precipitation solution (1 ml). After addition of the protein precipitation solution, the solutions were mixed by vortexing. Proteins were pelleted by centrifugation at 2,400 rpm for 10 minutes. The supernatant (containing the DNA) was transferred into a 15 ml tube containing 3 ml of isopropanol. The solutions were mixed by gentle inversion approximately 50 times. The tubes were spun at 2,400 r.p.m. for three minutes. The pellet size was observed and used to determine the appropriate amount of DNA hydration solution.

The supernatant was removed and the pellet was washed with 3 ml of 70% ethanol. The tubes were spun at 2,400 r.p.m. for 1 minute. The ethanol was removed. The pellet was resuspended in 1 ml 70% ethanol and transferred to a microfuge tube. The microfuge tube was centrifuged for 2 minutes at 14,000 g. The supernatant was removed and the pellet was allowed to air dry for 10 minutes.

DNA Hydration Solution was added to the DNA pellet. The DNA pellets were rehydrated overnight at room temperature or by incubation at 65° C. for one hour. The resuspended DNA was stored at 4° C. DNA concentrations were determined by spectrophotometric analysis of a diluted aliquot of the purified DNA.

Example 2

Oligonucleotide Synthesis

Oligonucleotides having the nucleotide sequences set forth in SEQ ID NOS:1-19, and 21-22 were designed. The oligonucleotides were synthesized by a commercial source. The synthetic oligonucleotides were resuspended at a concentration of 100 µM. The oligonucleotides were resuspended in water.

Example 3

Enzymatic Amplification of Multiple Regions of the Wiskott-Aldrich Syndrome Protein Gene PCR amplification is a process sensitive to contamination. Therefore PCR appropriate procedures were used to minimize the risks of contamination.

Master mixes for the PCR reactions were prepared. Master mixes contained 1.5 mM $MgCl_2$, 1×PCR buffer (Life Technologies Inc. Rockville, Md., USA), 0.2 mM dNTPs, 1.5 units Taq polymerase, 0.4 µM 5' primer, and 0.4 µM 3' primer. The master mix was prepared for the desired number of reactions plus two. Separate master mixes for each oligonucleotide pair were prepared.

PCR tubes were placed on ice. Aliquots of the master mix were transferred into the PCR tubes. Template DNA at 0.5 µg/reaction was added to each tube. The reaction tubes were placed in a thermocycler and the power was turned on. The PCR incubation conditions for the incubation periods were: 95° C., for 5 minutes; 35 cycles of 95° C., for 45 seconds, 57° C., for 45 seconds, and 72° C. for 1 minute, 45 and one incubation at 72° C. for 10 minutes. Following the 10 minute incubation at 72° C., the reactions were stored at 4° C. PCR product quality was assessed by agarose gel electrophoresis of an aliquot of the PCR reaction. In a preferred embodiment, the oligonucleotide pair having the nucleotide sequences set forth in SEQ ID NOS:21 and 22 was used to amplify exon 10. All six oligonucleotide pairs anneal at 57° C.

The amplified products of the PCR reaction were purified using the Qiaquick PCR Purification kit following the manufacturer's recommended protocol.

Example 4

Preparation of Amplified DNA Samples for Commercial Sequencing

Purified amplified DNA was obtained using the above described processes. Oligonucleotides were diluted to 3.3 µM. The nucleotide sequences of the sequencing primers are set forth in SEQ ID NOS:1-19 and 21-22. The primers set forth in SEQ ID NOS:1-12 and 21-22 were also used in the amplification reactions. It is recognized that a sequence reaction with each sequencing primer may not be necessary. For example, the sequence information obtained from a sequence reaction including a sequencing primer having a nucleotide sequence set forth in SEQ ID NO:21 or SEQ ID NO:22 may yield sufficient information to obviate the need for a sequence reaction including a sequencing primer having a nucleotide sequence set forth in SEQ ID NO:7 or SEQ ID NO:8.

Sequencing reaction mixtures were prepared. Each sequencing reaction contained 7 µl distilled, deionized $H_2O$. Two µl of the appropriate primer was added to each sequencing reaction tube. Three µl of purified PCR product obtained according to the methods described elsewhere above were added to each sequencing reaction tube. The samples were sequenced by a sequencing core facility (CHMC Sequencing Core). When the sequence data was obtained, the sequence information was compared with the Wiskott-Aldrich syndrome protein gene consensus nucleotide sequence. The Wiskott-Aldrich syndrome protein gene consensus nucleotide sequence (SEQ ID NO:20) is available in the NCBI (AF115549) and Celera (hCG19822) databases. Discrepancies between the patient's nucleotide sequence and the consensus sequence of the WASP gene indicate a mutation.

All publications, patents, and patent applications mentioned in the specification are indicative of the level of those skilled in the art to which this invention pertains. All publications, patents, and patent applications are herein incorporated by reference to the same extent as if each individual publication or patent application was specifically and individually incorporated by reference.

Although the foregoing invention has been described in some detail by way of illustration and example for purposes of clarity of understanding, it will be obvious that certain changes and modifications may be practiced within the scope of the appended claims.

That which is claimed:

1. An isolated nucleic acid molecule consisting of a nucleotide sequence selected from the group consisting of:
   (a) the nucleotide sequence set forth in SEQ ID NO:7 or SEQ ID NO:8.

2. An oligonucleotide pair comprising a first nucleic acid molecule and a second nucleic acid molecule, wherein said first nucleic acid molecule consisting of the nucleotide sequence set forth in SEQ ID No: 7 and wherein said second nucleic acid molecule consisting of the nucleotide sequence set forth in SEQ ID No: 8.

3. A kit for performing a method of amplifying a region of the Wiskott-Aldrich syndrome protein gene comprising an oligonucleotide pair consisting of:
   a first nucleic acid molecule consisting of the nucleotide sequence set forth in SEQ ID NO: 7 and a second nucleic acid molecule consisting of the nucleotide sequence set forth in SEQ ID NO: 8.

4. The kit of claim 3, further comprising 2, 3, 4, 5 or 6 oligonucleotide pairs selected from the group of oligonucleotide pairs consisting of:
   (a) a first nucleic acid molecule consisting of the nucleotide sequence set forth in SEQ ID NO: 1 and a second nucleic acid molecule consisting of the nucleotide sequence set forth in SEQ ID NO: 2;
   (b) a first nucleic acid molecule consisting of the nucleotide sequence set forth in SEQ ID NO: 3 and a second nucleic acid molecule consisting of the nucleotide sequence set forth in SEQ ID NO: 4;
   (c) a first nucleic acid molecule consisting of the nucleotide sequence set forth in SEQ ID NO: 5 and a second nucleic acid molecule consisting of the nucleotide sequence set forth in SEQ ID NO: 6;
   (d) a first nucleic acid molecule consisting of the nucleotide sequence set forth in SEQ ID NO: 9 and a second nucleic acid molecule consisting of the nucleotide sequence set forth in SEQ ID NO: 10;
   (e) a first nucleic acid molecule consisting of the nucleotide sequence set forth in SEQ ID NO: 11 and a second nucleic acid molecule consisting of the nucleotide sequence set forth in SEQ ID NO: 12;
   (f) a first nucleic acid molecule consisting of the nucleotide sequence set forth in SEQ ID NO: 21 and a second nucleic acid molecule consisting of the nucleotide sequence set forth in SEQ ID NO: 22;
   (g) a first nucleic acid molecule consisting of the nucleotide sequence set forth in SEQ ID NO: 1, SEQ ID NO: 3, SEQ ID NO: 5, SEQ ID NO: 9, SEQ ID NO: 11, or SEQ ID NO: 21; and a second nucleic acid molecule consisting of the nucleotide sequence set forth in SEQ ID NO: 2, SEQ ID NO: 4, SEQ ID NO: 6, SEQ ID NO: 10, SEQ ID NO: 12, or SEQ ID NO: 22.

5. The oligonucleotide pair of claim 2, wherein said first and second nucleic acid molecules allow amplification of a region of the Wiskott-Aldrich syndrome protein gene.

* * * * *

SEQUENCE LISTING

<160> NUMBER OF SEQ ID NOS: 22

<210> SEQ ID NO 1
<211> LENGTH: 18
<212> TYPE: DNA
<213> ORGANISM: Artificial Sequence
<220> FEATURE:
<223> OTHER INFORMATION: Synthetic oligonucleotide: WAS-1497

<400> SEQUENCE: 1
caagctcagc ctaacgag                                                    18

<210> SEQ ID NO 2
<211> LENGTH: 19
<212> TYPE: DNA
<213> ORGANISM: Artificial Sequence
<220> FEATURE:
<223> OTHER INFORMATION: Synthetic oligonucleotide WAS-12R2330

<400> SEQUENCE: 2
tgaggtcttg aagctatgg                                                   19

<210> SEQ ID NO 3
<211> LENGTH: 20
<212> TYPE: DNA
<213> ORGANISM: Artificial Sequence
<220> FEATURE:
<223> OTHER INFORMATION: Synthetic oligonucleotide-WAS 12.3241

<400> SEQUENCE: 3
ctccaaacca gactatgagg                                                  20

<210> SEQ ID NO 4
<211> LENGTH: 20
<212> TYPE: DNA
<213> ORGANISM: Artificial Sequence
<220> FEATURE:
<223> OTHER INFORMATION: Synthetic oligonucleotide: WAS-17R-4851

<400> SEQUENCE: 4
cttccattca ctcagctgtc                                                  20

<210> SEQ ID NO 5
<211> LENGTH: 22
<212> TYPE: DNA
<213> ORGANISM: Artificial Sequence
<220> FEATURE:
<223> OTHER INFORMATION: Synthetic oligonucleotide: WAS I7.5724

<400> SEQUENCE: 5
ctatactcat tcactcattc ag                                               22

<210> SEQ ID NO 6
<211> LENGTH: 22
<212> TYPE: DNA
<213> ORGANISM: Artificial Sequence
<220> FEATURE:
<223> OTHER INFORMATION: Synthetic oligonucleotide:
     WAS I9R.6327

<400> SEQUENCE: 6
gcgtatctta gctatgagct gc                                               22

<210> SEQ ID NO 7

```
<211> LENGTH: 21
<212> TYPE: DNA
<213> ORGANISM: Artificial Sequence
<220> FEATURE:
<223> OTHER INFORMATION: Synthetic oligonucleotide: WAS-I9.6318

<400> SEQUENCE: 7
ctaagatacg cactaagtca c                                              21

<210> SEQ ID NO 8
<211> LENGTH: 19
<212> TYPE: DNA
<213> ORGANISM: Artificial Sequence
<220> FEATURE:
<223> OTHER INFORMATION: Synthetic oligonucleotide: WAS-I10R.7015

<400> SEQUENCE: 8
aacctttcaa ccctatcac                                                 19

<210> SEQ ID NO 9
<211> LENGTH: 19
<212> TYPE: DNA
<213> ORGANISM: Artificial Sequence
<220> FEATURE:
<223> OTHER INFORMATION: Synthetic oligonucleotide: WAS-I10.6995

<400> SEQUENCE: 9
cagtgatagg gttgaaagg                                                 19

<210> SEQ ID NO 10
<211> LENGTH: 18
<212> TYPE: DNA
<213> ORGANISM: Artificial Sequence
<220> FEATURE:
<223> OTHER INFORMATION: Synthetic oligonucleotide: WASI11R.7343

<400> SEQUENCE: 10
ggctgatgtc actattgg                                                  18

<210> SEQ ID NO 11
<211> LENGTH: 22
<212> TYPE: DNA
<213> ORGANISM: Artificial Sequence
<220> FEATURE:
<223> OTHER INFORMATION: Synthetic oligonucleotide: WAS-I11.8701

<400> SEQUENCE: 11
tttgacaata tctcgactaa cc                                             22

<210> SEQ ID NO 12
<211> LENGTH: 18
<212> TYPE: DNA
<213> ORGANISM: Artificial Sequence
<220> FEATURE:
<223> OTHER INFORMATION: Synthetic oligonucleotide WAS-9121R

<400> SEQUENCE: 12
ggataacagc attggagg                                                  18

<210> SEQ ID NO 13
<211> LENGTH: 19
<212> TYPE: DNA
<213> ORGANISM: Artificial Sequence
<220> FEATURE:
<223> OTHER INFORMATION: Synthetic oligonucleotide: WAS-I1-1925

<400> SEQUENCE: 13
```
cgtcataatc cacccttcc                                                19

<210> SEQ ID NO 14
<211> LENGTH: 19
<212> TYPE: DNA
<213> ORGANISM: Artificial Sequence
<220> FEATURE:
<223> OTHER INFORMATION: Synthetic oligonucleotide: WAS-I1R-1943

<400> SEQUENCE: 14
ggaagggtgg attatgacg                                                19

<210> SEQ ID NO 15
<211> LENGTH: 18
<212> TYPE: DNA
<213> ORGANISM: Artificial Sequence
<220> FEATURE:
<223> OTHER INFORMATION: Synthetic oligonucleotide: WAS-I3-3492

<400> SEQUENCE: 15
ggagatggga aagttgcg                                                 18

<210> SEQ ID NO 16
<211> LENGTH: 21
<212> TYPE: DNA
<213> ORGANISM: Artificial Sequence
<220> FEATURE:
<223> OTHER INFORMATION: Synthetic oligonucleotide: WAS-14R-3729

<400> SEQUENCE: 16
catgagaggg gacttttcta g                                             21

<210> SEQ ID NO 17
<211> LENGTH: 22
<212> TYPE: DNA
<213> ORGANISM: Artificial Sequence
<220> FEATURE:
<223> OTHER INFORMATION: Synthetic oligonucleotide: WAS16R-4105

<400> SEQUENCE: 17
cccatccatc agtccacaca tc                                            22

<210> SEQ ID NO 18
<211> LENGTH: 20
<212> TYPE: DNA
<213> ORGANISM: Artificial Sequence
<220> FEATURE:
<223> OTHER INFORMATION: Synthetic oligonucleotide: WAS-I6-4498

<400> SEQUENCE: 18
acacacagat ttccctcaag                                               20

<210> SEQ ID NO 19
<211> LENGTH: 19
<212> TYPE: DNA
<213> ORGANISM: Artificial Sequence
<220> FEATURE:
<223> OTHER INFORMATION: Synthetic oligonucleotide: WAS-I8-6058

<400> SEQUENCE: 19
ttgtctcctc gccttattc                                                19

<210> SEQ ID NO 20
<211> LENGTH: 9484
<212> TYPE: DNA

```
<213> ORGANISM: Homo sapiens
<220> FEATURE:
<221> NAME/KEY: exon
<222> LOCATION: (1667)...(1798)
<220> FEATURE:
<221> NAME/KEY: exon
<222> LOCATION: (2096)...(2236)
<220> FEATURE:
<221> NAME/KEY: exon
<222> LOCATION: (3360)...(3446)
<220> FEATURE:
<221> NAME/KEY: exon
<222> LOCATION: (3547)...(3649)
<220> FEATURE:
<221> NAME/KEY: exon
<222> LOCATION: (3759)...(3800)
<220> FEATURE:
<221> NAME/KEY: exon
<222> LOCATION: (3894)...(3947)
<220> FEATURE:
<221> NAME/KEY: exon
<222> LOCATION: (4594)...(4768)
<220> FEATURE:
<221> NAME/KEY: exon
<222> LOCATION: (5867)...(5909)
<220> FEATURE:
<221> NAME/KEY: exon
<222> LOCATION: (6113)...(6266)
<220> FEATURE:
<221> NAME/KEY: exon
<222> LOCATION: (6473)...(6879)
<220> FEATURE:
<221> NAME/KEY: exon
<222> LOCATION: (7133)...(7247)
<220> FEATURE:
<221> NAME/KEY: exon
<222> LOCATION: (8920)...(8975)

<400> SEQUENCE: 20
ctgcagtgtt gctcccaaca gcaagaacca gaagcagccc aaagggctgt tacaggagaa      60
tatggacacc caggctgcac atgcacacca tggaatgctg tatggcagtg gaaataaatg     120
aacagctacc actataggca aacaggaatc acagcaacag ccaagagtga aggcgtggag     180
ggacgagacc atgcactcac acctggcctg cctggctcgc actccgggca aagggggtcag    240 aacagtgact ggcacacacg ttaagtgcta tgtgagtgtt aagataaaac taggatgtcc     300
agtggggaga aagcaagcct ttgaagatta tgtgctttta caaacttcaa gtgcaatgaa     360
aactaaacaa gatgttgttc aggcattcat atatgatata aagttccttt ctttaaaaaa     420
gggatgggct gggcacggtg gctcacgcct gtaattctaa tactttggga ggccgaggca     480
ggtggatcac gaggtcgaga atcgagacc atcctggcca acatggtgaa accctgtctc     540
tactaaaaat acaaaaaaat tagctgggcg tggtggcgtg tgcctgtagt cccagctact     600
tgggaggctg aggcaggaga gtcacttgaa cccgggaggc aaaggttgca gtgagccgag     660
atcgtgccac cgcactccag cctggcgaca gagtgagact ccatctcaaa aaaaaaaga     720 aaaaaaaaag tatgacaagc agaaagtaat ttggagctg cggggaggca agggtaaggg     780
atggggaagt ggaccagagg catatgcgtc attggcagtg tctaagcact cacgataggc     840
gtggatcaca ggggctcgct ctgtaattaa aaggaaaagg gttttttgttg tgttgttgtt    900 gttgctgttt ttgagacaag ggtcttgctc tgtcatcatc caggctggag tgcagtggtg     960
cagtctcagc tcactgcaac ctccgcctcc tgggttcaag cgattctcct gcctcagcct    1020
cctgagcagc taggactaca ggtgtgtgcc accatgcctg gctaattttt gtattttta    1080 gtggaaatgg ggttttgcca tgttgcccag gctcgtcttg aactcctgac ctcaagtgat    1140
ccactcgtct cggcctccca aagtgctggg attacaggtg tgagctattg tccccagcca    1200
```

```
aaaggaaaag ttttactgta gtaacccttc cggactaggg acctcgggcc tcagcctcag    1260
gctacctagg tgctttagaa aggaggccac ccaggcccat gactactcct tgccacaggg    1320
agccctgcac acagatgtgc taagctctcg ctgccagcca gagggaggag gtctgagcca    1380
gtcagaagga gatgggcccc agagagtaag aaaggggag gaggacccaa gctgatccaa     1440
aaggtgggtc taagcagtca agtggaggag ggttccaatc tgatggcgga gggcccaagc    1500
tcagcctaac gaggaggcca ggcccaccaa ggggcccctg gaggacttgt ttcccttgtc    1560
ccttgtggtt ttttgcattt cctgttccct tgctgctcat tgcggaagtt cctcttctta    1620
ccctgcaccc agagcctcgc cagagaagac aagggcagaa agcaccatga gtggggcccc   1680
aatgggagga aggcccgggg gccgaggagc accagcggtt cagcagaaca taccctccac    1740
cctcctccag gaccacgaga accagcgact ctttgagatg cttggacgaa aatgcttggt    1800
gagctgggga tctcctgccc ccgccccgtc ccaccgtttt cttcctcttc ctctcctcct    1860
tctctctctt cccctcctcc cgctcctcct ttccctctcc atcatctcct ctcctagaat    1920
ttcccgtcat aatccaccct tcccaggaag atctcaatgt ctacttgcct tccctctggc    1980
tgcagctctt cctttgggcc catgactgtc atgaggcagg aaggaccagg tctggctcca    2040
agaccttgtg gctaccctg accagactcc actgaccct gctttcctct cccagacgct      2100
ggccactgca gttgttcagc tgtacctggc gctgcccct ggagctgagc actggaccaa     2160
ggagcattgt ggggctgtgt gcttcgtgaa ggataacccc cagaagtcct acttcatccg    2220
cctttacggc cttcaggtga ccccccaccc cccgactgga cttgcaagcc agttctcaac    2280
ccgcaaaccc agatctgtgt ccatatgtgt ccatagcttc aagacctcag acctgatcag    2340
tgaatccctg agccccagaa ccaaagactc atccagatgg caaactctga cttgcctttc    2400
taagtctgca atgactggcc ccagtctccg tatcaagatc tctaaagccc ccagtattag    2460
tctgctgcct aagcctaatc ttttccacaa attccaataa atgagcactg tatttgtacc    2520
tgaacctcaa atctattcta aactcaacat tttgcatccc aggaatctct catcaaaact    2580
cctgaacccc agatgtttgc caagctccta agtcataaat ctgttcaaca aaccccaaag    2640
ttgaatattc cattgatcct tgaactccaa atctgtcctt ctaaatccac agcacagacc    2700
ccagagttcc catattaaaa ttcctgaaca ctcaaatacc gaggtagttc ttaagcaaaa    2760
agtcttttcc acaatcccct gacctgaact ttctaggttt aagccccaaa ttcatccttt    2820
taaacccata aagatggacc cagcataact tccagatccc aaggctatca aatatccacc    2880
aaactcctaa accataactc tctccacaaa ccccaaattg cacttacttt agctggactc    2940
cccgcgaaac tcccaagtct atgtgtctga acttcaaatc tcaactccaa cccccaaata    3000
ctagaatcct acctgtcatg aattggggct ggggtggtgg gggagggcat ggattgaatc    3060
tgtgaatgag cctcaacttc ctaagactag agtcctaaat tatgaaattc aagcccccaa    3120
gtcccagatc tagggcccca accccaaat ccaaacctct cacaaaagtg tatggctccc     3180
agactatacc ccacaatcca cacccttaga caccaactct ctggtgctga gctgaaaatc    3240
tccaaaccag actatgaggc tcccaaatcc agacaccctg ctccctgccc agctaacaaa    3300
agcctgccac cccggcgtg cctcagtgcc actgtgcctc caccctaca cctctccagg      3360 ctggtcggct gctctgggaa caggagctgt actcacagct tgtctactcc accccaccc     3420 ccttcttcca caccttcgct ggagatgtaa gtgatcaacc agccctcggg cctcacttgg    3480
ggtgtggaga ggagatggga aagttgcggg ggacctggga ggcggctgac cccaaggtat    3540
```

```
gtgcaggact gccaagcggg gctgaacttt gcagacgagg acgaggccca ggccttccgg    3600
gccctcgtgc aggagaagat acaaaaaagg aatcagaggc aaagtggagg tgaggaggcc    3660 acagggagg  aaaggaagtt gggcagaggt gagtgcaagc ctggggaact agaaaagtcc    3720
cctctcatgg tcctggctcc caatccatct atccacagac agacgccagc tacccccacc    3780
accaacacca gccaatgaag gtgagtcctc tagtgcaagt aggggtaata aggggctagc    3840
ccaggaacct gtggcagggc tgtgataact ctctacacat tccatcttcc cagagagaag    3900
aggagggctc ccacccctgc ccctgcatcc aggtggagac caaggaggtg cgtgctgatt    3960
cttccctgtg tctctggatg gatgggtaag agtggatgga ggaatgagga gttggatggg    4020
tgcctaagtg ggtgaatgga taggtagatt gataggtatg tggatggacg agcgggtgca    4080
tggatgtgtg gactgatgga tgggtggatg gattggcggc agatggctga gtagagggat    4140
gaattgatgg gaggatgaaa gtctaagtag atagatgcat aggtgaatgg gtatgtggat    4200
aaatgaatga aaaggtagat ggatgactga gtaaattaat caatgagtga atgaatgaac    4260
agtgaataaa tgactaaatg acaagtttca gtcagtgaag aaagcatgat tgaatgaata    4320
aatgagtaaa tgaatatttt aacaaattca ttagtcaatg agccagtgaa tgataaagca    4380
tgagggaatg aaaacatgaa tgaatcagtg aatgtatgaa tggtttgtgg gatccaccca    4440
cttctccata gaccctactt gaacccttca cccactacct ccatgaccat caacacaca    4500 cacagatttc cctcaaggct tccgtttctt gcccctgtgc tttggttggt tggtaagtgg    4560
gtcaatgagc caaccaccct attttcccca caggccctcc agtgggtccg ctctccctgg    4620
ggctggcgac agtggacatc cagaaccctg acatcacgag ttcacgatac cgtgggctcc    4680
cagcacctgg acctagccca gctgataaga aacgctcagg gaagaagaag atcagcaaag    4740
ctgatattgg tgcacccagt ggattcaagt gagagccact ccccagtgga cccacagatt    4800
cctgggggca gaggggcaca tgaacaagtg gacagctgag tgaatggaag gatgggcaga    4860
tgggcacatg gctgggtggc tgagtgggta aatgggtggt tggataggta ggtgcagggc    4920
tgggtctagg gagaggtaaa taaggcacca agggtacaaa atttaaggag gcactcactc    4980
tcagaggcat gcaactgtaa ttcctgactc tcagagtgag tgactcactt aaattttgca    5040
ccctaggcac cttacttgcc tcaccctggg cccactctgg gtgggctgtt aggagagcag    5100
gtgggtgggc aggtgaacaa atggatagat agatgaggta gatgatggat gagaagggct    5160
ggtgggtagg tgggtgagtg gatgggtgga tggatggata aatgaatgga tgaatgaatg    5220
ggttgaagaa tgaatggata agtggttgga tggacaagtt tatgggtgga tgggttgatg    5280
ggaggtgcgt ggatagatag atgggtgagt ggataggtgt gtggacagat tgatatgcag    5340
gctgattggc tcacagacaa ggtggatggg gatggacagg tggacagata cgtggatgaa    5400
tggacagttc aatggataag tgaacagaag tgtgtggttg catgggtaga aaaatgagtg    5460
gatggataga tggaaaggtg ggcacatggg taggtggatg ggtggatgga caagtgtgtg    5520
tgaggacaga ctggtggaca aatgggtgaa cagacatatg tgggcagata gttgcagaga    5580
cagatgtatg gacagatcag tagtccaaca gatgaatgtg aatgataggg tggacaaatg    5640
catgggatag atggggaaag agggatgggt ggatggatca gcaccacaaa ctatggagcc    5700
cttctaattc cataactcct gcctatactc attcactcat tcagtctcat tcattaattc    5760
tggcccctca gagtctcttt gggcaggaga gggcaagagg gtttcactat gaagggaggg    5820
aaggaagggc agtgaggatt cactggagtc tcttcacctc tcccaggcat gtcagccacg    5880
tggggtggga ccccagaat ggatttgacg tgagtaactt cagagtctct tggactccac    5940
```

```
taaacttcca cccacccttc caaagaccac tgctgagacc ccaccccag atcgtgccct      6000 tcccacaccc ctctcagatc ccttgctggg atggacccaa cgacaatcca tgtcgcttgt      6060
ctcctcgcct tattcctcta ctcctgcccc tggccttttt cctcctgggc aggtgaacaa      6120
cctcgaccca gatctgcgga gtctgttctc cagggcagga atcagcgagg cccagctcac      6180
cgacgccgag acctctaaac ttatctacga cttcattgag gaccagggtg ggctggaggc      6240
tgtgcggcag gagatgaggc gccagggtga gaccctgctt ccatacgctc ccttctctag      6300
cccaagcagc tcatagctaa gatacgcact aagtcactca gtccttatgg gagcacctat      6360
actgcttcag tcaggagttg gtcagtgggg gtacccattt tacaaatgag caaaactgag      6420
gctcagaaga aatcaatgag agttacagct atgtgttata cccctccac agagccactt       6480 ccgccgcccc caccgccatc tcgaggaggg aaccagctcc cccggccccc tattgcgggg      6540
ggtaacaagg gtcgttctgg tccactgccc cctgtacctt tggggattgc ccacccccca      6600
ccaacacccc ggggaccccc accccaggc cgaggggggcc ctccaccacc accccctcca      6660
gctactggac gttctggacc actgcccct ccacccctg gagctggtgg gccacccatg       6720
ccaccaccac cgccaccacc gccaccgccg cccagctccg ggaatggacc agcccctccc      6780
ccactccctc ctgctctggt gcctgccggg ggcctggccc ctggtggggg tcggggagcg      6840
cttttggatc aaatccggca gggaattcag ctgaacaagg tgaggacagg caggatggag      6900 gattggggt ctaggactct ggggtgtccc gtctaagtca ggatactggg gggctgaggc       6960
caggactgag gagagtgcca ggccttaggg attcagtgat agggttgaaa ggttggtggg      7020
aagccttgaa ggggactgga gtgtgtggga gagaaaatat tgatggaggg gcggggagaa      7080
atgctccttt cccaggccct aagccctctg tgctgatccc tgcctgctgc agaccccttgg      7140 ggccccagag agctcagcgc tgcagccacc acctcagagc tcagagggac tggtgggggc      7200
cctgatgcac gtgatgcaga agagaagcag agccatccac tcctccggtg agctgatcct      7260
gccggggcct caaacctggc tcccagggct agcactggcc tcaaaacaat cccagcagtc      7320
accaccaata gtgacatcag ccccatctgt ttgacagcat taacatgaat cttgtgtcag      7380
cctcgttttt gacaatgtta acattaagtc attatgtgac aataatataa ttaactccaa      7440 cttttgacagt aatattaaca ttaatgccag ggtgtgtcca caatattaat gtcattccca     7500
catgttcagt actactaaca tcagctggcc gggcgcggtg gctcatgcct gtaatccagg      7560
aactttggga ggctaaggca ggaggatcac ttgagcccag gagttcgaga ccagcctggg      7620
caatatagtg agacctcgtt tccataaaaa ctaaattcaa aaaagtagt caagcatagt        7680 ggtgtgtgcc tgtggtccca gctacttggg aggctgaggt gggaggattg cttgacccctg     7740 ggaggtcaag gcagcagtga tccatgattg tgccactgca ctccagcctg ggtgacagag      7800
atcctatctc aaaaaaaaaa aaaattaacc cattatgtga tgacaatatt atgaagaaca      7860
ctattgttga caatattaat tttaattcca tgtattaaca gatttacatt aattcattat      7920 gacgtaaccct aatctaatct tttaaaaaat ttttttgaaa cagggtctcg ctctgtgtcc     7980
caggctggag tacagtggtg caatcatggc tcagtgcagc ctcaacctcc caggctcaag      8040
cgatcctccc gcctcagctc ccaaagtagc tgggactaca ggcgtgtgcc accatacctg      8100
gctaattttt ggtgtttttt tggtagtgat gagctctcac taccaagctc tcactactct      8160
catgttgccc aggctgctct gcaactccag ggctcaagcg atctgccccg cctcagcctc      8220
ccagagtgct gggattacag gcatgagcca ccaggcctgg ctgttaacct atctttttat      8280
```

-continued

```
aataatgtta ctattactct cttaatctgt cagcaatact gtcactaatc cattatatga      8340
tgcaatatta gtatcaacct actataggaa cttcatcttt cgacaatgat tttttttttt      8400
cttttgagac ggagtcttgg tctgtcaccc aggctggagt gcagtggcgc gatcttggct      8460
aactgcagac tctgcctcct gggttcaagc gattctcctg cctcagcctt ccgagtagct      8520
gggactacag gcacgccact acgcccagct aattttgatg ttattgtcat taacccccatt    8580 atgtgtcaaa atattagcg ttaaccagac aggaagcaat aatatattat cacacctttg       8640
ctaatattat ttaaattcac cctattatgt gataaatagg ttaacattaa ccctttgttt     8700
gacaatatct cgactaacca catttttgac agcataaact tcaactccaa ctagaactca     8760
gaccccaact ataatccctt tcttgtccca aatggaaact ctaacttgcc ctcctctagc     8820
atgagacctc agaaccccag ggtccagtcc tcacctccca ggccctatga agcccccac      8880 caacctccca gggcatctta tctttctctt tccctccaga cgaaggggag gaccaggctg     8940
gcgatgaaga tgaagatgat gaatgggatg actgagtggc tgagttactt gctgccctgt    9000
gctcctcccc gcaggacatg gctcccccctc cacctgctct gtgcccaccc tccactctcc   9060
tcttccaggc ccccaacccc ccatttcttc cccaccaacc cctccaatgc tgttatccct    9120
gcctggtcct cacactcacc caacaatccc aaggcccttt ttatacaaaa attctcagtt    9180
ctcttcactc aaggattttt aaagaaaaat aaaagaattg tctttctgtc tctctataaa    9240
tctcagtctg tttacattcc aaatgtggga atgggtccc tttcccccaa agtccctttt    9300
attcatttat cccattttat ttatttagac ttacatgtat atattcattc attcatttat    9360
tccctcagtc atttagcctg tatttctttg tttccttctg cccctctgtc tttcaacatt   9420
tattgtcagg tactatttta ggggctagga atcaagaagt gggaaaaaaa acagacaaga   9480
attc                                                                  9484
```

<210> SEQ ID NO 21
<211> LENGTH: 19
<212> TYPE: DNA
<213> ORGANISM: Artificial Sequence
<220> FEATURE:
<223> OTHER INFORMATION: Synthetic oligonucleotide WAS I10R-7017

<400> SEQUENCE: 21

```
ccaacctttc aaccctatc                                                   19
```

<210> SEQ ID NO 22
<211> LENGTH: 18
<212> TYPE: DNA
<213> ORGANISM: Artificial Sequence
<220> FEATURE:
<223> OTHER INFORMATION: Synthetic oligonucleotide WAS I9-6271

<400> SEQUENCE: 22

```
agaccctgct tccatacg                                                    18
```